US 6,796,513 B2

(12) United States Patent
Fraccaroli

(10) Patent No.: US 6,796,513 B2
(45) Date of Patent: Sep. 28, 2004

(54) NEBULIZER VIAL FOR AEROSOL THERAPY

(75) Inventor: Nicola Fraccaroli, Desenzano del Garda (IT)

(73) Assignee: Med 2000 S.p.A., Padenghe sul Garda (IT)

( * ) Notice: Subject to any disclaimer, the term of this patent is extended or adjusted under 35 U.S.C. 154(b) by 0 days.

(21) Appl. No.: 10/344,362

(22) PCT Filed: Aug. 7, 2001

(86) PCT No.: PCT/EP01/09105
§ 371 (c)(1),
(2), (4) Date: Feb. 11, 2003

(87) PCT Pub. No.: WO02/13895
PCT Pub. Date: Feb. 21, 2002

(65) Prior Publication Data
US 2003/0192962 A1 Oct. 16, 2003

(30) Foreign Application Priority Data
Aug. 11, 2000 (IT) .................................. MI2000A1887

(51) Int. Cl.[7] .......................... A61M 11/06; A61M 11/00
(52) U.S. Cl. .............. 239/338; 128/200.18; 128/200.21
(58) Field of Search ...................... 128/200.18, 200.14, 128/200.21; 239/338, 340, 390, 518, 524

(56) References Cited

U.S. PATENT DOCUMENTS

| 3,836,079 | A | | 9/1974 | Huston .................. 128/200.18 |
|---|---|---|---|---|
| 5,054,477 | A | | 10/1991 | Terada et al. .......... 128/200.14 |
| 5,165,392 | A | | 11/1992 | Small, Jr. .............. 128/200.18 |
| 5,235,969 | A | * | 8/1993 | Bellm .................... 128/200.18 |
| 5,287,847 | A | | 2/1994 | Piper et al. ............ 128/200.18 |
| 5,503,139 | A | | 4/1996 | McMahon et al. ..... 128/200.18 |
| 5,755,218 | A | * | 5/1998 | Johansson et al. ..... 128/200.14 |
| 6,338,443 | B1 | * | 1/2002 | Piper ..................... 128/200.18 |
| 2002/0157663 | A1 | * | 10/2002 | Blacker et al. ........ 128/200.21 |

FOREIGN PATENT DOCUMENTS

DE          1046264          12/1958

* cited by examiner

Primary Examiner—Thomas Denion
Assistant Examiner—Thai-Ba Trieu
(74) Attorney, Agent, or Firm—Young & Thompson

(57) ABSTRACT

The nebulizer vial for aerosol therapy comprising a tube fed at a first end with compressed air, the tube being constricted at its second end prior to the relative exit orifice to obtain a venturi effect. The orifice of the tube emerges from the free surface of a solution of an aerosol therapy medicament, a nozzle being concentrically mounted on the second end of the tube such that between the tube and nozzle there remains an interspace communicating with the solution. A flow breaker device is provided above the orifice of the nozzle. The vial is provided with an exit for the formed aerosol and an inlet for entry of external air as a result of suction exerted by the patient on the exit. For diameter parity of the orifice of the nozzle, elements are provided to vary the distance between the nozzle orifice and the flow breaker device.

14 Claims, 1 Drawing Sheet

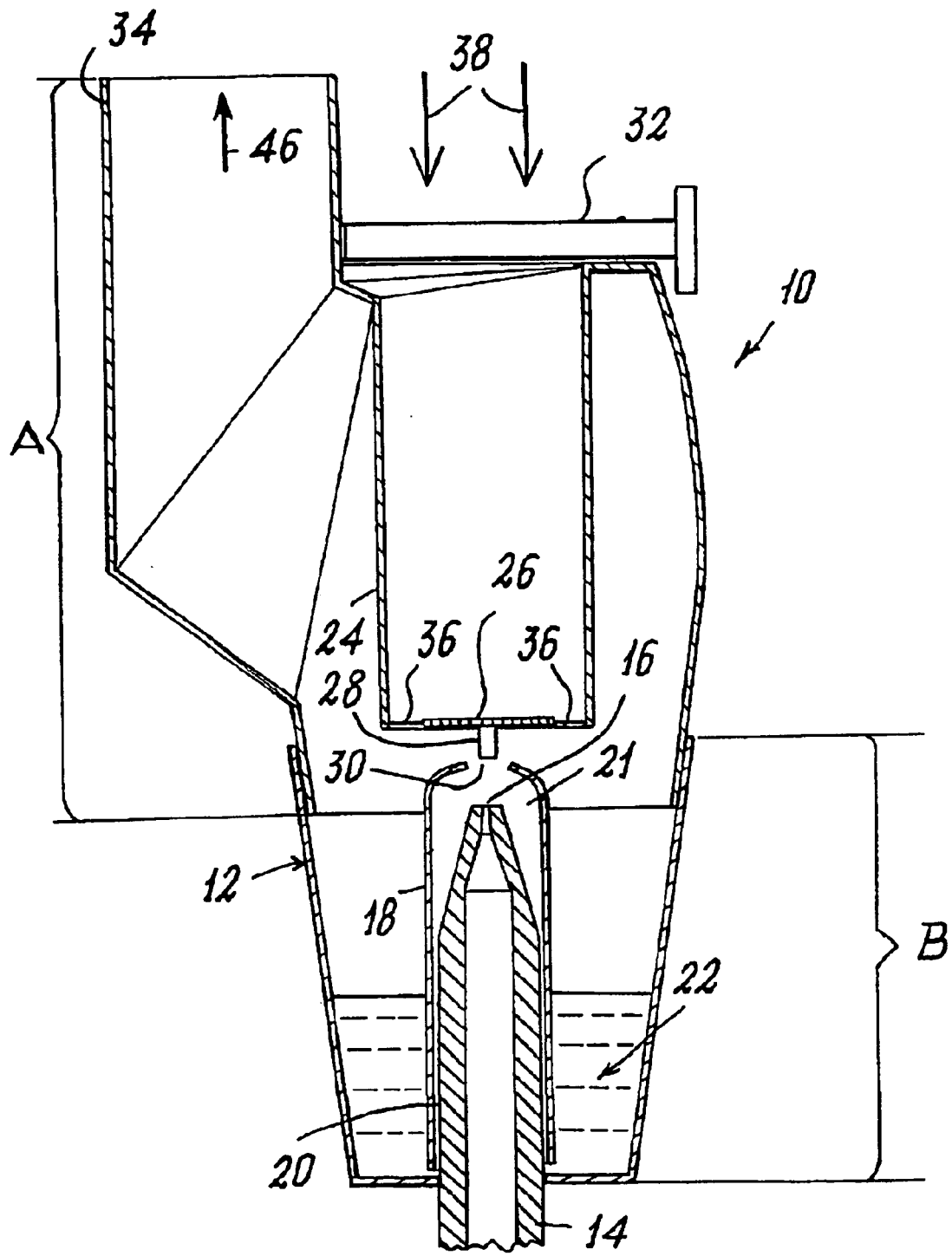

NEBULIZER VIAL FOR AEROSOL THERAPY

CROSS REFERENCE TO RELATED APPLICATION

This is the 35 USC 371 national stage of International Application PCT/EP01/09105 filed on Aug. 7, 2001, which designated the United States of America.

BACKGROUND OF THE INVENTION

Known nebulizer vials for aerosol therapy are of plastic construction and use the venturi principle, in particular the so-called double venturi, in the sense that the air originating from a compressor is passed at high velocity through a small-diameter tube constricted internally (to form the venturi) and terminating with an orifice which emerges from the free surface of a solution of an aerosol therapy medicament contained in a reservoir. A nozzle is mounted concentrically on the end of said tube such that between the nozzle and the tube, there is an interspace communicating lowerly with the solution contained in the reservoir. The compressed air leaving the orifice of said tube causes the particles or droplets of the medicament solution to be sucked upwards through said interspace, to form an upwardly directed stream of solution particles, which leaves the nozzle orifice. The stream of solution particles formed in this manner is atomized (to form the aerosol) by causing the stream to strike against a flow breaker device positioned above the nozzle orifice. The flow breaker device is positioned at, but without completely closing, the lower end of a conduit through which external air can enter the vial following inhalation by the patient on an aerosol exit conduit with which the vial is provided.

As known to the expert of this sector, the characteristic parameters of a therapeutic aerosol are the mass median aerodynamic diameter (indicated by the initials MMAD which depends on the orifice diameter of the nozzle), the geometric standard deviation (indicated by the initials GSD) and the nebulization rate.

The MMAD provides an indication of the average dimensions of the particles forming the aerosol, this identifying the region of the air passageways in which the nebulized medicament will deposit.

The GSD enables the degree of dispersion of the solution particle dimensions within the distribution to be evaluated.

Finally, the nebulization rate is essentially an index of the mass of medicament nebulized per unit of time.

The MMAD and the GSD can both be obtained from the aerosol particle diameter distribution: the MMAD is in fact the aerodynamic diameter to which 50% of the aerosol particle diameter distribution corresponds; the GSD can be calculated from the particle diameter distribution graph, if the distribution is sufficiently linear between 10% and 90%, i.e. if the distribution is Gaussian, by using suitable extrapolation calculation methods (see ISO 9276-2).

The medical literature has established that, for therapeutic purposes, those regions of a patient's respiratory tract reachable by the aerosol are related to the dimensions of the medical solution particles inhaled. More precisely, aerodynamic particle diameters greater than 5 microns are adequate for treatment of the upper air passages; diameters between 2 and 6 microns for the tracheobronchial region; diameters between 0.5 and 3 microns for alveolar administration. Reference should be made to the following texts for further details:

International Commission on Radiological Protection (1994): Human respiratory Tract Model for Radiological Protection. Annals of the ICRP Vol. 24, No. 1–3 Elservier Science Inc. Tarrytown N.Y.

Heyder J., Gebhart J., Rudolf G., Schiller C. F. and Stahlhofen W. (1986): Deposition of particles in the human respiratory tract in the size range 0.005–15 $\mu m$ Journal of Aerosol Science 17(5):811–825.

Stahlhofen W., Rudolf G., and James A. C. (1989): Intercomparison of Experimental Regional Deposition Data. Journal of Aerosol Medicine 2(3): 285–308.

From the aforegoing it is evident that to treat respiratory affections it is important that the dose of suitable medicament is administered only into the therapeutically appropriate region of the respiratory tract, to prevent wastage of medicament in addition to undesired systemic effects. To achieve this, a nebulizer vial must be used which is able to generate an aerosol of the precise particle size distribution characteristics.

SUMMARY OF THE INVENTION

An object of the present invention is therefore to provide a nebulizer vial for aerosol therapy which enables the MMAD to be varied.

It is also important that a nebulizer vial has a nebulization rate suitable for the type of patient to be treated. In this respect, although it is true that increasing the nebulization rate accelerates the therapy, a high nebulization rate, although suitable for normal adult patients, can be excessive for determined patients such as children or seriously asthmatic patients, to the extent of making correct administration of the medicament difficult.

Another object of the invention is therefore to provide a nebulizer vial of the aforestated type in which the nebulization rate can be varied.

As a nebulizer vial for aerosol therapy is often used for domiciliary treatment by non-expert persons and can be used repeatedly for different respiratory pathologies, a further object of the invention is to provide a vial of the aforesaid type in which the aerosol characteristics (particle size distribution and nebulization rate) can be varied on the basis of the patient's therapeutic needs in a very simple manner within the ability of any patient.

The aforestated first object is attained by the nebulizer vial of the present invention, characterised in that, for diameter parity of the nozzle orifice, means are provided to vary the distance between the nozzle orifice and the flow breaker device. The flow breaker device may comprise a flow breaker diaphragm. In this respect, it has been verified that varying this distance varies the MMAD of the solution particles.

The means for varying said distance can comprise (for a predefined orifice diameter of the nozzle) nozzles of different length, to mount on the end of the compressed air tube (the flow breaker diaphragm being fixed), so also varying in consequence the distance between the orifice of the compressed air tube (which is always in the same position) and the orifice of the nozzle. Obviously, various series of nozzles can be provided which differ in the orifice diameter of the nozzles.

As an alternative the same nozzle can again be used, but with a means which, with one and the same nozzle fixed to the compressed air tube, enables either the elevation of the compressed air tube orifice to be varied (and consequently the elevation of the nozzle orifice), or the position of said flow breaker diaphragm to be varied relative to the compressed air tube orifice maintained in a fixed position.

Preferably on that surface of the flow breaker diaphragm facing the nozzle orifice there is provided coaxial with the nozzle orifice a peg which, on replacing the nozzle with another of different length or by vertically moving the flow breaker diaphragm (if the nozzle is not replaceable), approaches the nozzle orifice to a greater or lesser extent.

The aforestated second object is attained by providing a device for adjusting the flow of external air entering the vial as a result of inhalation by the patient, this enabling the nebulization rate of the nebulizer vial to be adjusted.

To attain the aforesaid final object the nebulizer vial is formed in two parts, of which a lower part contains the solution of medicament for aerosol therapy and comprises the compressed air feed tube and the relative nozzle, whereas the upper part comprises the flow breaker diaphragm, the inlet enabling external air to enter the vial following inhalation by the patient, and the aerosol exit conduit, the two parts being removably connected together.

The fact of forming the nebulizer vial in two parts as just described can be used to vary the distance between the nozzle orifice and the flow breaker diaphragm, the two said parts of the vial then being formed and connected together in such a manner as to be able to obtain different distances between the nozzle orifice and the flow breaker device.

BRIEF DESCRIPTION OF THE DRAWINGS

The invention will be more easily understood from the ensuing description of one embodiment thereof. In this description reference is made to the accompanying drawing, in which the single FIGURE represents a very schematic vertical section through a nebulizer vial of the invention, the section being taken on a plane passing through the axis of the compressed air feed tube.

DETAILED DESCRIPTION OF THE INVENTION

Observing the FIGURE it can be seen that the nebulizer vial 10 is composed of two parts, namely an upper part A and a lower part B. To enable the vial 10 to be used, the parts A and B have to be connected together (as shown in the FIGURE), this being achievable in various ways, for example by a screw connection, by a bayonet connection or by a snap clip connection.

As can be seen, the outer casing 12 of the part B is shaped as a cup, the base of which is sealedly traversed by a tube 14 for feeding compressed air generated by a compressor (not shown) of the conventional type used for aerosol apparatus. The upper end of the tube 14 is tapered both externally and internally (the internal taper causing the said venturi effect), the tube 14 finally terminating with an exit orifice 16.

A nozzle 18 is mounted concentrically on the upper end of the tube 14 so that between the nozzle and the tube, there remains an interspace 20 which lowerly communicates with a solution 22 of a determined medicament which occupies, to a determined level, the lower part of the cup-shaped casing 12, which hence acts as a reservoir for the medicament solution. To center the nozzle 18 about the tube 14, this latter or the nozzle 18 can be provided with radial spacer ribs (not shown for simplicity). In the illustrated example, between the upper end of the compressed air tube 14 and the corresponding inner surface of the nozzle 18 there exists a free space 21 which acts as a preatomization chamber.

Above the nozzle 18 and coaxial thereto there is disposed a conduit 24, the lower end of which is partly closed by a bar-shaped flow breaker diaphragm 26, the two ends of which are connected to the conduit 24. At the upper end of the conduit 24 there is provided a regulator device which comprises a flow regulator cock shown very schematically and indicated overall by 32. The flow regulator cock 32 enables the nebulization rate to be continuously adjusted from a minimum value to a maximum value, in order to adapt the aerosol leaving the vial to the respiration characteristics of the patient. In the FIGURE the arrows 38 indicate the entry of external air resulting from the suction exerted by the patient on the upper end of an aerosol exit channel with which the nebulizer vial 10 is provided. A usual mouthpiece, a respiratory mask or a nasal adapter (not shown) through which the patient can inhale the aerosol can be connected to this upper end.

In the illustration example the bar 26 carries a peg 28, coaxial to the nozzle 18, which extends downwards and approaches the orifice 30 of the nozzle 18.

As already stated, one way of varying the MMAD of the particles of the aerosol produced by the vial 10 is to provide interchangeable nozzles 18 of different length such that the distance between the orifice 30 of the nozzle 18 and the diaphragm 26 varies in accordance with the length of the nozzle 18. In the illustrated example the presence of the peg 28 enables not only said distance but also the aperture of the orifice 30 to be varied, this enabling the best results to be obtained. Another way of varying said distance is to make the compressed air tube 14 insertable to a greater or lesser extent (for this purpose reference markings can be provided thereon) into the cup-shaped casing 12 of the lower part B, so that the orifice 30 of the nozzle 18 (which in this case is fixed to the tube 14) approaches the diaphragm 26 to a greater or lesser extent. Another simple way of adjusting said distance is to construct the casing of the vial 10 in such a manner that the two parts A and B can be inserted or screwed into each other to a greater or lesser extent in order to achieve this object. As a variant, a number of spacing connection stubs having different heights can be provided between the two parts A and B. Again, the external air conduit 24 (to the lower end of which the diaphragm 26 is fixed) can be made vertically movable relative to the rest of the vial 10, within determined limits, to enable said distance to be varied.

According to one embodiment of the invention, a vertical section through the vial 10 taken on a plane passing through the axis of the exit orifice 16 has an outer profile which is at least approximately elliptical, the minor axis of the ellipse passing through or in proximity to the orifice 30 of the nozzle 18.

Although already apparent from the aforegoing, the operation of the nebulizer vial 10 will now be briefly described.

After pouring the prescribed quantity of medicament solution 22 into the cup casing 12 of the lower part B (having obviously separated the two parts A and B) and reassembling the two parts A and B, the compressed air compressor (not shown) is operated so that the compressed air reaches the lower end of the tube 14. As already stated, the exit of compressed air from the orifice 16 of the tube 14 causes particles of solution to be drawn through the interspace 20, to form an ascending stream of air and solution particles which leaves from the orifice 30 of the nozzle 18 and strikes the diaphragm 26, to cause atomization of the solution particles. As a result of the sucking action exerted by the patient through the upper end of the aerosol exit channel 34—causing external air to be drawn through the conduit 24 upperly provided with a suitably flow regulator cock—the aerosol stream, formed as a result of the impact of the solution particles against the diaphragm 26 and their mixing with the air entering through the conduit 24 and the apertures 36, is directed towards the exit channel 34, to finally reach the patient who, as stated, exerts the sucking action through a mouthpiece, mask or nasal adapter.

From the aforegoing it is apparent that the particle size characteristics of the aerosol can be varied very simply directly by the patient. The patient simply separates the two parts A and B of the vial 10, and can then position in the vial 10 that nozzle 18 of appropriate length to obtain the required MMAD, or replace the existing nozzle 18 with one suitable for the particular therapy to be carried out. It is also apparent that if the other aforesaid solutions for varying the distance between the orifice 30 of the nozzle 18 and the diaphragm 26 are adopted, this distance can again be varied very simply.

What is claimed is:

1. A nebulizer vial for aerosol therapy, comprising:

a tube fed at a first end with compressed air, the tube being constricted at its second end prior to an exit orifice to obtain a venturi effect, the orifice of the tube emerging from the free surface of a solution of an aerosol therapy medicament;

a nozzle being concentrically mounted on the second end of the tube such that between the tube and nozzle, there remains an interspace communicating with the solution;

a flow breaker device being provided above an orifice of the nozzle;

an aerosol exit channel for formed aerosol and a conduit for entry of external air as a result of suction exerted by a patient on the aerosol exit channel;

wherein, for diameter parity of the orifice of the nozzle, means are provided for varying the distance between the nozzle orifice and the flow breaker device;

said means for varying the distance between the orifice of the nozzle and the flow breaker device comprising a series of interchangeable nozzles of different lengths.

2. The nebulizer vial for aerosol therapy as claimed in claim 1, wherein the means for varying the distance between the orifice of the nozzle and the flow breaker device comprise means enabling the elevation of the flow breaker device to be varied relative to the orifice of the nozzle, with said orifice of the nozzle being fixed.

3. The nebulizer vial for aerosol therapy as claimed in claim 1, wherein the means for varying the distance between the orifice of the nozzle and the flow breaker device comprise means enabling the elevation of the exit orifice of the compressed air tube to which the nozzle is fixed to be varied, with the flow breaker device being fixed.

4. The nebulizer vial for aerosol therapy as claimed in claim 1, wherein the flow breaker device comprises a diaphragm disposed above the orifice of the nozzle.

5. The nebulizer vial for aerosol therapy as claimed in claim 4, wherein the diaphragm is disposed at one end of the conduit without however closing said end, the other end of the conduit being open towards the outside to enable external air to enter following suction exerted by the patient on the aerosol exit channel.

6. The nebulizer vial for aerosol therapy as claimed in claim 4, wherein a lower face of the diaphragm facing the orifice of the nozzle comprises a downwardly extending peg coaxial to the orifice and partly closing the orifice.

7. The nebulizer vial for aerosol therapy as claimed in claim 1, wherein a regulator device is provided for the external air entering through the conduit.

8. The nebulizer vial for aerosol therapy as claimed in claim 7, wherein the regulator device comprises a flow regulator cock.

9. The nebulizer vial for aerosol therapy as claimed in claim 1, comprising two parts, wherein a lower part contains the aerosol medicament solution and comprises the tube and the nozzle; wherein an upper part comprises the flow breaker device, the conduit, and the aerosol exit channel; and said two parts being removably connectable together.

10. The nebulizer vial for aerosol therapy as claimed in claim 9, wherein the means for varying the distance between the orifice of the nozzle and the flow breaker device comprise means enabling the two parts to be connected together to obtain different distances between the orifice and the flow breaker device.

11. The nebulizer vial for aerosol therapy as claimed in claim 10, wherein the means which enables the two parts to be connected together to obtain different distances between the orifice and the flow breaker device comprises a series of spacing connection stubs between the two parts; said stubs having different heights.

12. The nebulizer vial for aerosol therapy as claimed in claim 1, wherein a preatomization chamber is provided between the second end of the tube and the corresponding inner surface of the nozzle.

13. The nebulizer vial for aerosol therapy as claimed in claim 1, wherein a vertical section through the vial taken on a plane passing through the axis of the orifice has an outer profile which is at least approximately elliptical, the minor axis of the ellipse passing through or in proximity to the orifice of the nozzle.

14. The nebulizer vial for aerosol therapy as claimed in claim 1, wherein on a given nozzle length, a series of nozzles having different diameters of the orifice is provided.

* * * * *